Figure 1:
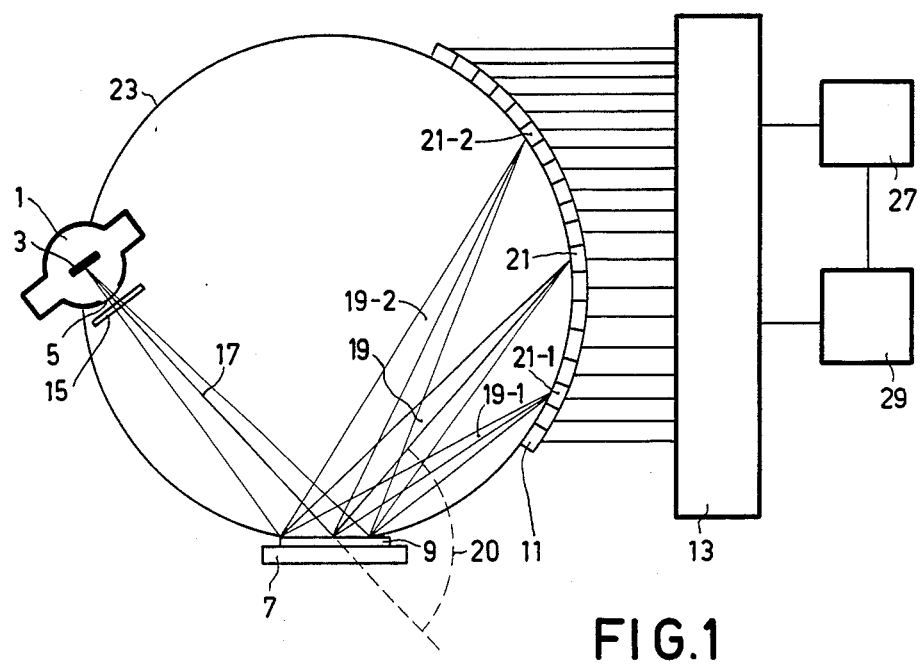

United States Patent [19]

Houtman et al.

[11] Patent Number: 4,800,580
[45] Date of Patent: Jan. 24, 1989

[54] X-RAY ANALYSIS APPARATUS

[75] Inventors: Eliberthus Houtman, Almelo; Geert Brouwer, Eindhoven, both of Netherlands

[73] Assignee: U.S. Philips Corporation, New York, N.Y.

[21] Appl. No.: 921,861

[22] Filed: Oct. 20, 1986

Related U.S. Application Data

[63] Continuation of Ser. No. 573,244, Jan. 23, 1984.

[30] Foreign Application Priority Data

Feb. 4, 1983 [NL] Netherlands ............... 8300419

[51] Int. Cl.$^4$ .......................................... G01N 23/20
[52] U.S. Cl. ........................................ 378/71; 378/83; 378/84; 250/370.01
[58] Field of Search ............... 378/19, 51, 70, 91, 378/71, 72, 82, 83, 84; 250/370 R, 370 GX, 370 H, 370 L, 370 I

[56] References Cited

U.S. PATENT DOCUMENTS

| | | | |
|---|---|---|---|
| 3,663,812 | 5/1972 | Koenig | 378/83 |
| 3,852,594 | 12/1974 | Paolini | 378/81 |
| 3,896,313 | 7/1975 | Berman et al. | 250/370 |
| 3,934,138 | 1/1976 | Bens | 378/79 |
| 3,973,128 | 8/1976 | Le May | 378/91 |
| 4,066,900 | 1/1978 | Le May | 378/19 |
| 4,131,794 | 12/1978 | Bruninx | 378/83 |
| 4,504,962 | 3/1985 | Moore | 378/19 |

FOREIGN PATENT DOCUMENTS 2345406 7/1975 Fed. Rep. of Germany.
2628493 12/1977 Fed. Rep. of Germany ........ 378/19

OTHER PUBLICATIONS

Dierker et al., "Image Intensifier Gamma Camera with a Position-Sensitive Silicon Stripe Detector", Siemens Forsch-U. Entwickl.-Ber. Bd. 6 (1977), Nr. 4.

*Primary Examiner*—Craig E. Church
*Assistant Examiner*—John C. Freeman
*Attorney, Agent, or Firm*—Paul R. Miller

[57] ABSTRACT

In an X-ray analysis apparatus provided with a detector comprising photodiode-detection elements, it is possible to eliminate the dark current and the background current from the measurement signals due to the fact that elements in the signal reading device can be combined. Due to the fact that also during the measurement at a stationary peak beside the signal amplitude also signal ratios can be obtained from combinations of detector elements, the correct position and amplitude of the peaks to be measured can be determined. The detector can also be provided with mutually separated detector elements which have such a surface area and configuration that the dark surrent can already be compensated thereby.

21 Claims, 3 Drawing Sheets

X-RAY ANALYSIS APPARATUS

This is a continuation of application Ser. No. 573,244, filed Jan. 23, 1984.

The invention relates to an X-ray analysis apparatus comprising an X-ray source for producing an X-ray beam for irradiating a specimen to be examined and a detector device for detecting radiation emanating from the specimen.

Such an X-ray apparatus in the form of an X-ray powder diffractometer is known from U.S. Pat. No. 3,852,594. In the diffractometer described therein, a specimen is irradiated by an X-ray beam starting from a comparatively narrow elongated focus. Radiation diffracted in the specimen is measured by an X-ray detector. For this purpose, an entrance slit for the detector is situated in an imaging plane of the diffracted X-ray beam and a collimator is situated in the beam path of the diffracted X-ray beam. For measuring a diffractogram, the detector is moved along the arc of a circle. During this rotation, the specimen is also rotated about the axis of rotation of the detector, the detector rotating at an angular velocity which is twice that of the specimen. Thus, a diffractogram is obtained. The accuracy of the angular position of the specimen with respect to a radiation object point and, though to a slightly lesser extent, with respect to the detector is then directly determinative of the accuracy of the measurement. The mechanism of rotation therefore has to operate very precisely and the collimater and the entrance slit of the detector have to be invariably positioned and adjusted to the optimum. For a detailed description of such a mechanism of rotation, reference is invited to Philips Technical Rev., No. 27, pages 300–310.

The invention has for its object to provide an X-ray analysis apparatus in which without a loss of resolution other detection means are used which permit a wider choice in detection methods.

For this purpose, according to the invention, an X-ray analysis apparatus of the kind mentioned in the opening paragraph is characterized in that the detection device comprises a composite photodiode - semiconductor detector of which various detector elements can be connected individually or in combination to a signal reading device.

Photodiodes, such as silicon photodiodes, can be manufactured without great difficulty in various forms and dimensions and have a high stability even after a prolonged irradiation by X-ray quanta. For signal reading, direct use can be made of operational amplifiers. Photodiodes for measuring electromagnetic radiation as such are known, but these devices are usually adapted to count pulses and not to measure directly the photo-current produced by the incident radiation.

By adaptation of the diode dimension which is determinative of the resolution of an apparatus equipped with such diodes, it can now be achieved, for example, that this resolution is determined by an effective detector cell width instead of by a mechanical detector slit. Thus, for example, in a powder diffractometer equipped with an adapted diode detector an at least equal resolution can be realized by means of a simpler and less expensive apparatus. An X-ray spectrometer can be constructed in a corresponding manner without a loss of resolution in a less expensive and simpler way. The dimension of the diodes is defined during the manufacture and can be adapted without further expedients to an optical radiation system. By an electronic combination of several photodiodes arranged beside each other, a stepwise adjustment of the slit width can be obtained, which, for example, can also replace the usual slit exchange for various measurements. By a suitable combination of photodiodes or by an adapted construction of a photodiode as such, the influence of the temperature-dependent dark current of the photodiodes in the measurement results can be reduced sufficiently.

In a preferred embodiment, the detection device comprises a series of silicon photodiodes, for example in the form of elements having an effective width of 0.05 mm and a length of 10 mm. The width dimension is now determinative of the resolution of the apparatus and a desired detection entrance width of the detector can be adjusted by combination of elements arranged beside each other. A larger width then yields a stronger detection signal, but a lower resolution, and conversely. By combination of detector elements and an adapted processing of combined signals thus obtained, the background current and the dark current can be eliminated from the measurement results. By means of a guard diode, the influence of photons incident upon the boundary region of the effective detector surface can be eliminated. Further, asymmetrical spectral lines can be converted into symmetrical spectral lines by an adapted convolution process. Such a conversion may also be realized directly by giving the photodiode-detector an effective surface area in accordance with the diaphragm described in DE No. 2,345, 406. This can be achieved not only by combination of detector elements, but also by allotting to the photodiode elements a weighting factor adapted for the measurement or directly by adapting the construction of the photodiodes. The effective surface area of the photodiode-detector then effectively constitutes a replica of an intensity distribution to be measured in the relevant radiation line.

In a preferred embodiment in the form of a spectrometer, a simpler apparatus can be realized with a focusing optical system while using an array of silicon photodiodes. The apparatus can consequently become considerably less expensive without the quality being adversely affected, which has the optical advantage that the photodiodes themselves act as detection entrance slit for the radiation to be measured.

In a further preferred embodiment in the form of a powder X-ray diffractometer operating according to the Bragg-Brentano principle, the detector further comprises at least a photodiode. More particularly, the detector system, which is normally equipped with a detector slit and a, for example, gas-filled detector, can then be replaced by a photodiode-detector.

A preferred embodiment is constituted by a so-called simple position diffractometer, such as a focusing diffractometer, in which no moving parts are used. In this case, the specimen occupies a fixed position and the detector movement is neutralised by the use of a position-sensitive detector, for which an array of photodiodes is particularly suitable.

Figure 2:
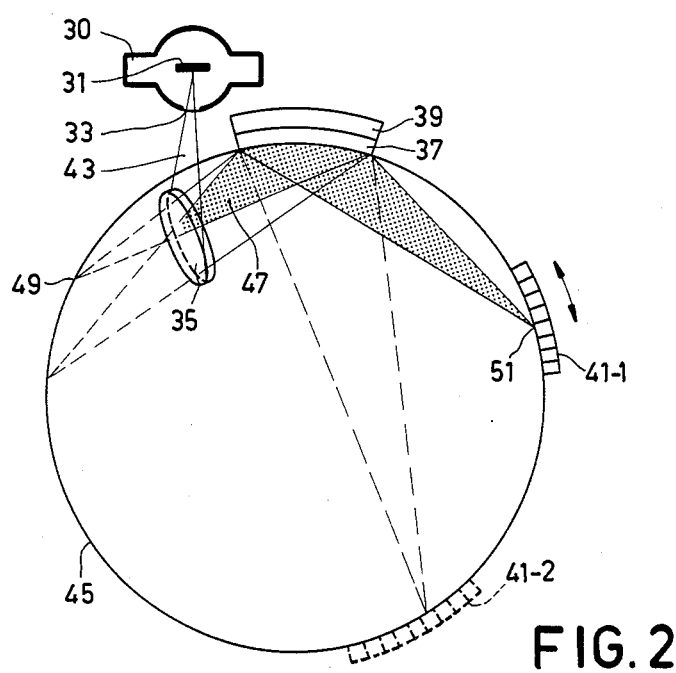
Figure 3:
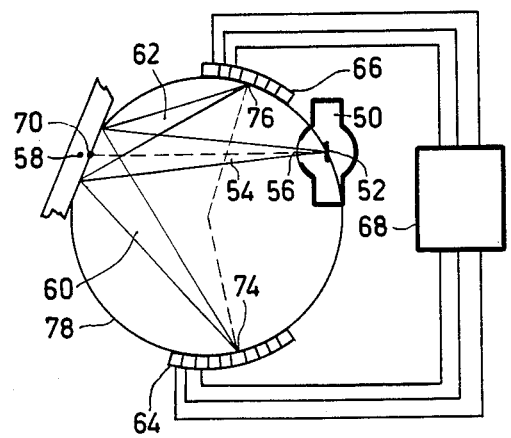

A few preferred embodiments according to the invention will now be described more fully with reference to the drawing. In the drawing:

FIG. 1 shows in outline a focusing powder diffractometer according to the invention, FIG. 2 shows in outline a focusing X-ray spectrometer according to the invention, FIG. 3 shows an outline of an arrangement for measuring material stresses and texture according to the invention, and FIGS. 4(a–e) show a few preferred embodiments of photodiode-detectors for X-ray analysis apparatus according to the invention.

For an X-ray powder diffractometer, an X-ray source 1 having an anode 3 and an exit window 5, a polycrystalline specimen 9 mounted on a specimen support 7 and a detector 11 equipped with a signal reading system 13 are shown in FIG. 1. A radiation beam 17 to be emitted by the X-ray tube 1 and passing, for example, through a nickel filter 15, which beam substantially comprises K radiation after passing the filter, diffracts at the specimen a part 19 at an angle $2\theta$. This part of the beam is trapped by a detector cell 21 of the detector. In the Figure diffracted beams 19-1 and 19-2 are illustrated for a few series of crystal surfaces; these beams are trapped by detector cells 21-1 and 21-2. This may also be effected by the detector cell 21 which meanwhile has rotated. When the anode 3 of the X-ray tube and the specimen 9 are located on a focusing sphere 23, the beam 19 will be focused on this sphere. Therefore, the detector also is arranged so as to coincide with the circle 23. Depending upon the crystal structure, different diffraction lines are thus formed on the detector and a diffractogram can be recorded. For example, information about the crystal structures present in the specimen can be obtained from the diffractogram.

For displaying measurement data, a writer or monitor 27 can be connected to the signal reading device 13, while for storing measurement data a storage device 29 can be connected to this reading device. For any digital processing or storage, analogue-to-digital converter may be added. In this case, the detector is composed of, for example, silicon photodiode elements which have in front elevation, i.e. viewed from the incident X-ray beam 19, an effective width of, for example, 0.05 mm and a length of, for example, 10 mm. Viewd in the direction of width, a detector element can be composed, as will be described more fully hereinafter, of several adjacent elements to be read in combination. A detector comprises, for example, 200 such photodiode elements. The photodiodes are covered on the entrance side, for example, for protection from incident environmental light with a window which is transparent to the radiation to be detected and consists, for example, of beryllium. The array of photodiodes can be arranged in an inner surface of a strip of silicon which may be spherical. The array may alternatively be composed of a plurality of units planar in themselves which each comprise, for example, 24 photodiodes arranged beside each other. A plurality, for example, twenty, of these units then constitute 480 contiguously arranged detector channels along an arc of a quasi circle. Because of the fact that the detector is effective only in an extremely thin layer, no disadvantageous consequences are obtained by any oblique incidence of the radiation into the detector due to this construction.

FIG. 2 shows of an X-ray spectrometer an X-ray source 30 having an anode 31 and an exit window 33, a specimen 35, a double focusing crystal 37 mounted in a holder 39 and a detector 41. The X-ray source 30 irradiates the specimen 35 with an X-ray beam 43. Depending upon the wavelength, parts of the fluorescence radiation produced in the specimen and characteristic of the irradiated elements, for which the Bragg-relation is satisfied, are trapped and focused by the crystal 37 in a line on a focusing sphere 45. Thus, for example, a part 47, which is limited by marginal rays, is focused to the crystal of an object line 49 associated with the relevant wavelength in a focusing line 51. The position of the relevant focusing line on the sphere cross-section 45 is consequently dependent upon the wavelength of the fluorescence radiation produced in the specimen and characteristic of an element present in the specimen. By means of the detector 41, the intensity of the diffracted radiation can be detected in a position-sensitive manner. For this purpose, the detector, which also in this case is composed of silicon photodiodes, can be moved along the sphere cross-section 45. During the detection, also in this case additional information can be acquired by combination of detector elements, as will be described hereinafter.

FIG. 3 shows very schematically an X-ray diffraction apparatus for measuring macro-material stresses. Since by means of this X-ray analysis apparatus distances between successive crystal surfaces are defined, for example, the pure strain in the crystals can be analysed thereby. In stress measurements, there is started from this information. It is preferably desired of an apparatus used for this purpose that it can carry out measurements comparatively rapidly and that it is transportable. The transportability is especially required for measurements on, for example, parts of large work pieces and the like. The accuracy of the measurements must not be adversely affected by the fact that this requirement is satisfied because the crystal deviations obtained due to macro-stresses are mostly comparatively small. For this apparatus FIG. 3 shows an X-ray source 50 having an anode 52 for producing an X-ray beam 54, by which a specimen 58 can be irradiated through an exit window 56. The specimen 58 can be considered to form part of a larger entire structure to be examined. In known apparatus of this type, described, for example, in U.S. Pat. No. 3,934,138, for detecting X-ray beams emanating from the specimen, such detectors are used which are constructed as position-sensitive ionization chambers. A disturbing effect is then exerted by the position-dependent defocusing occurring in the apparatus and by the oblique incidence of the X-ray beam to be measured. According to the invention, the apparatus shown is provided with a first photodiode-detector 64 and a second photodiode-detector 66 which are connected to a signal processing device 68. Due to the fact that effective surfaces of the photodiodes of detectors 64 and 66 can readily be given a cylindrical form and these detectors, as already stated, are substantially insensitive to the direction in which the beam is incident, the disadvantages do not occur in this case. Due to the construction of the detector elements as such or due to electronic combination of cells, an optimum effective detection width can be chosen, with which a line shift occurring due to any macro-material stresses can be measured. The detectors can be simply adapted for the optimum positioning and in this case coincide with a focusing circle 78, on which are located the anode 52, a tangent point 70 of the specimen and the focus lines 74 and 76 of the beams 60 and 62. For a further embodiment of an apparatus for these measurements reference is made to the embodiment of FIG. 5 of the co-pending U.S. patent application Ser. No. 573,250, filed Jan. 23, 1984, and assigned to the same assignee.

FIGS. 4 (a–e) show various examples of the detector devices according to the invention having several photodiode cells to be read in combination.

Figure 4A:
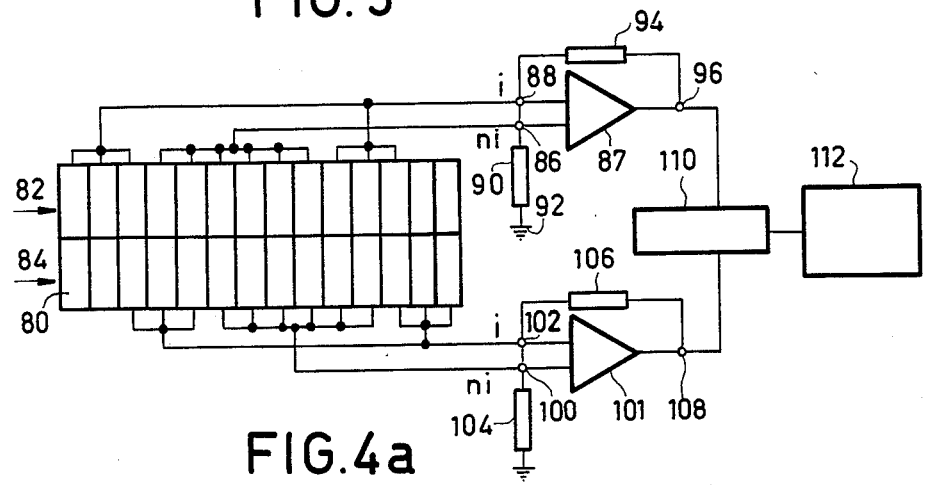

FIG. 4a shows such a detector comprising in this case a series of fourteen adjacent detector elements 80 having, for example, per element a width of 0.05 mm and a length of 10 mm. The overall width of the detector entrance slit then becomes 0.7 mm. This width can be adapted to the requirements by the use of a different number of detector elements or a different width dimension per element. In this case, the detector is further divided. in accordance with the drawing, into an upper series of photodiodes 82 and a lower series of photodiodes 84. Such a division can be realized in a simple manner when the photodiodes are formed in the semiconductor material. Of the upper series, in this case six centrally arranged photodiodes are together connected to a non-inverting input 86 of an operational amplifier 87, while the photodiodes located on either side thereof on the outer side are together connected to an inverting input 88 of the operational amplifier 87. The non-inverting input is usually connected via a resistor 90 to a point of fixed potential, or ground 92, while a resistor 94 connects the inverting input 88 to an output 96 of the operational amplifier 87. The lower series of photodiodes are combined in a corresponding manner, but now, for example, the whole is shifted by two cells. Thus, six centrally arranged photodiodes are connected to a non-inverting input 100 of an operational amplifier 101, while adjoining two times three photodiodes are together connected to an inverting input 102 of the operational amplifier 101. The non-inverting terminal of the amplifier 101 is connected through a resistor 104 to a point of fixed potential, while the inverting input 102 is connected through a resistor 106 to an output 108 of the amplifier. Both the output 96 and the output 108 are connected to an electronic signal reading processing device 110, to which is connected a recording/reproducing device 112. By means of such a detector device, by combination of the distinct overall signals, the background current and the dark current can be eliminated from the ultimate measurement signal and a peak shift can be found from quasi second derivation signals. The correct position for the relevant peak can be determined from the ratio between the two signals and by means thereof the amplitude in situ for the peak can be derived.

Figure 4B:
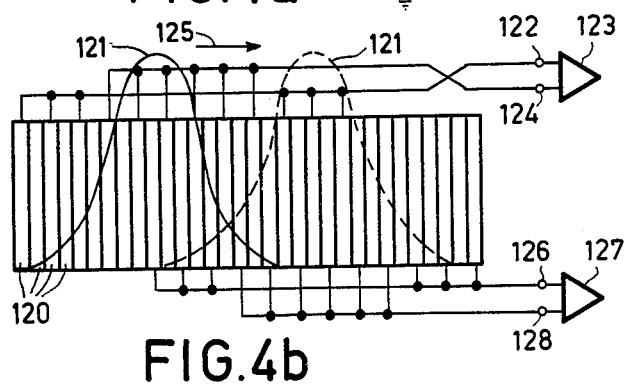

FIG. 4b shows a detector circuit arrangement in which detector elements 120 are not subdivided. The detector elements also in this case are connected groupwise to an inverting input 122 of an operational amplifier 123, to a non-inverting input 124 thereof, to an inverting input 126 of an operational amplifier 127 and to a non-inverting input 128 thereof, respectively. Without subdividing in the direction of height, in accordance with the drawing, the photodiode elements, also in this case background current and dark current can be eliminated and a peak shift can be found by second derivation measurement. Of a peak 121 to be measured, two positions are indicated by a full line and a dotted line, respectively. During measuring, the peak 121 is consequently displaced in the direction of the arrow 125.

Figure 4C:
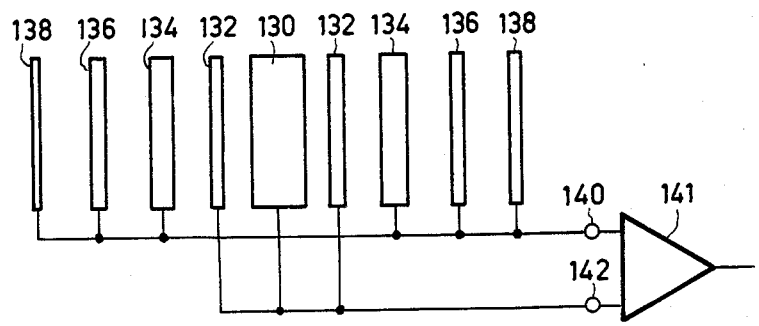

FIG. 4c shows an embodiment of a detector with which the corrections can be carried out more directly and exact second derivation signals can be measured. While maintaining an overall width, viewed in the direction of width of a usual line profile, of, for example, 0.5 mm, due to different widths of the elements the effective surface area of in this case the centrally arranged elements 130 plus two times 132 together is equal to the effective surface area of all the elements in off-centered positions two times 134 plus two times 136 plus two times 138. The centrally arranged elements are again together connected to, for example, an inverting input 142, while elements in off-centered positions are together connected to a non-inverting input 140 of an operational amplifier 141.

Figure 4D:
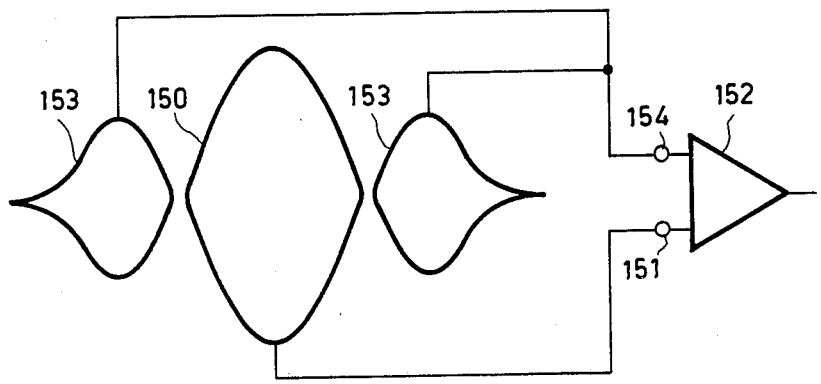

With a detector form as shown in FIG. 4d, the form of the active detector surfaces already meets the desire to be able to carry out an exact peak-position measurement. However, the condition is then imposed that the energy distribution of the radiation beam to be measured, viewed in the direction of height in the drawing, is homogeneous. For the measuring process, the central part 150 is connected, for example, to an inverting input 151 of an operational amplifier 152, while the two edge portions 153 are connected to a non-inverting input 154 of this amplifier. According to the embodiments described with reference to FIGS. 4c and 4d, an effective detector surface corresponding to the diaphragm described in DE No. 2,345,406 for converting an asymmetrical peak into a more symmetrical peak can also be formed in the semiconductor material.

Figure 4E:
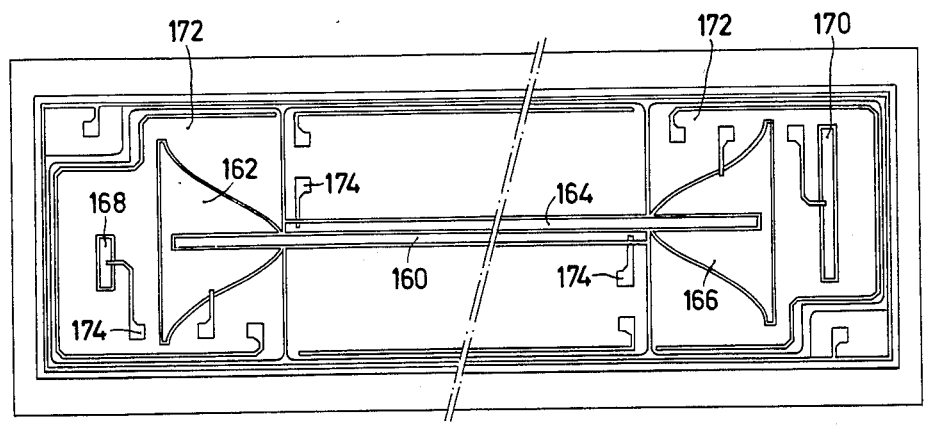

A silicon photodiode-detector of the kind shown in FIG. 4e has four active detector regions, a detector strip proper 160, a bell-shaped region 162, a second detector strip 164 and a second bell-shaped region 166. The strips 160 and 164 have, for example, dimensions of $0.1 \times 8$ mm$^2$. The surface area of each of the strips is equal to the surface area of the associated bell-shaped region. As a result, it is achieved that the dark currents of the strip and of the bell-shaped region are equal on first approximation. As far as a difference would nevertheless occur therein due to differences other than differences in surface area, this can be compensated for by additional active regions 168 and 170 which are formed in the silicon and have, for example, a surface ratio of 1:3 and can be connected at will to the inverting or the non-inverting input, as a result of which an additional possibility for compensation of the dark current is obtained. As a last compensation step a control is possible by relatively varying the voltages present for draining charge carriers not belonging to the signal between guards 172 and the active detection surfaces, as a result of which, the effective boundary between the two strips is shifted, albeit over only a small distance. For external connection, the various regions, guards etc. are provided with connections 174.

All compensation means together permit obtaining under all measuring conditions an optimum compensation, as a result of which the temperature compensation can invariably be complete A favourable additional effect is that a background signal which varies linearly in position over the width of the active part of the device is also switched off.

If desired, for measuring narrow peaks, there may be measured with one of the strips 160 and 164 individually, and for wider peaks measurements may be made with both strips together. The change-over between the two situations can be realized in a simple manner in the reading device and may be effected automatically. Due to the fact that the absolute surface area of the peaks measured is zero due to the negative parts on either side thereof, the variation in the detection system, which is connected with a large time constant, can be compensated for by a d.c. blocking RC coupling. In this case, however, the beam has to cover both the strips and the bell-shaped regions.

When the bell-shaped regions are screened at least in part, for example, by lead laminations, the signal with background can be measured while maintaining the temperature compensation.

Photodiode-detectors according to the invention can also be used successfully in a diffractometer of high resolution to be utilized for measuring on single crystals, for example, for measuring diffusion phenomena. For an extensive description of such a diffractometer, reference is invited to U.S. patent application Ser. No. 548,274, filed Nov. 3, 1983, and assigned to the same assignee.

What is claimed is:

1. An X-ray analysis apparatus comprising
   an X-ray diffractometer comprising:
   X-ray source means for producing X-rays,
   a specimen to be examined being irradiated by said X-rays,
   detector means for detecting X-radiation emanating from said specimen, said detector means including a plurality of detector elements, each of said detector elements being a composite photodiode-semiconductor detector element for directly measuring photocurrent produced by said X-radiation, and
   signal reading means receiving signals from said composite photodiode-semiconductor detector elements for reading said signals, said composite photodiode-semiconductor detector elements being connected to said signal reading means in either a separate connection from each of said composite photodiode-semiconductor detector elements to said signal reading means or a connection of groups of said composite photodiode-semiconductor detector elements connected to said signal reading means,
   wherein said composite photodiode-semiconductor detector elements have a resolution determined by detection entrance widths of said composite photodiode-semiconductor detector elements, and
   wherein adjacent ones of said detector elements are joined to determine said entrance widths.

2. An X-ray analysis apparatus according to claim 1, wherein said plurality of photodiode-semiconductor elements provide a structure for a combined entrance slit width and detecting function.

3. An X-ray analysis apparatus according to claim 2, wherein said signal reading means includes operational amplifiers.

4. An X-ray analysis apparatus according to claim 3, wherein said detection entrance widths are provided in the form of a line profile to be measured.

5. An X-ray analysis apparatus according to claim 1, wherein said composite photodiode-semiconductor elements include silicon photodiodes.

6. An X-ray analysis apparatus according to claim 5, wherein each of said silicon photodiodes have an effective width dimension of 0.05 mm and a length of 10 mm.

7. An X-ray analysis apparatus according to claim 5, wherein said detector elements include 200 of said photodiode-semiconductor elements.

8. An X-ray analysis apparatus according to claim 1, wherein said detection entrance width of said detector elements are in a peak-width direction of said X-radiation from said specimen, said detector elements being provided in a series of said elements.

9. An X-ray analysis apparatus according to claim 8, wherein said detection entrance widths correspond to a half-value width of peaks to be measured.

10. An X-ray analysis apparatus according to claim 1, wherein said groups of said detector elements are electrically connected to obtain both signal amplitude measurements and signals for peak-shift measurements by combination of signals from said groups.

11. An X-ray analysis apparatus according to claim 1, wherein said detector elements obtain optimum temperature compensation under all measuring conditions.

12. An X-ray analysis apparatus comprising
    an x-ray spectrometer comprising:
    a double focussing monochromatizing crystal,
    a specimen to be examined being irradiated by said X-rays,
    detector means for detecting X-radiation diffracted by said specimen, said detector means including a plurality of detector elements, each of said detector elements being a composite photodiode-semiconductor detector element for directly measuring photocurrent produced by said X-radiation, and
    signal reading means receiving signals from said composite photodiode-semiconductor detector elements for reading said signals, said composite photodiode-semiconductor detector elements being connected to said signal reading means in either a separate connection from each of said composite photodiode-semiconductor detector elements to said signal reading means or a connection of groups of said composite photodiode-semiconductor detector elements connected to said signal reading means,
    wherein said composite photodiode-semiconductor detector elements have a resolution determined by detection entrance widths of said composite photodiode-semiconductor detector elements, and
    wherein adjacent ones of said detector elements are joined to determine said entrance widths.

13. An X-ray analysis apparatus according to claim 12, wherein said signal reading means includes operational amplifiers.

14. An X-ray analysis apparatus according to claim 12, wherein said detection entrance widths are provided in the form of a line profile to be measured.

15. An X-ray analysis apparatus according to claim 12, wherein said composite photodiode-semiconductor elements include silicon photodiodes.

16. An X-ray analysis apparatus according to claim 15, wherein each of said silicon photodiodes have an effective width dimension of 0.05 mm and a length of 10 mm.

17. An X-ray analysis apparatus according to claim 15, wherein said detector elements include 200 of said photodiode-semiconductor elements.

18. An X-ray analysis apparatus according to claim 12, wherein said detection entrance width of said detector elements are in a peak-width direction of said X-radiation from said specimen, said detector elements being provided in a series of said elements.

19. An X-ray analysis apparatus according to claim 18, wherein said detection entrance widths correspond to a half-value width of peaks to be measured.

20. An X-ray analysis apparatus according to claim 12, wherein said groups of said detector elements are electrically connected to obtain both signal amplitude measurements and signals for peak-shift measurements by combination of signals from said groups.

21. An X-ray analysis apparatus according to claim 12, wherein said detector elements obtain optimum temperature compensation under all measuring conditions.

* * * * *